(12) United States Patent
Bharat et al.

(10) Patent No.: US 11,109,776 B2
(45) Date of Patent: Sep. 7, 2021

(54) QUANTIFYING PROBE DEFLECTION FOR IMPROVED CATHETER IDENTIFICATION

(71) Applicant: KONINKLIJKE PHILIPS N.V., Eindhoven (NL)

(72) Inventors: Shyam Bharat, Cortlandt Manor, NY (US); Cynthia Ming-fu Kung, New York, NY (US); Jochen Kruecker, Washington, DC (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1013 days.

(21) Appl. No.: 14/415,825

(22) PCT Filed: Jul. 22, 2013

(86) PCT No.: PCT/IB2013/056000
§ 371 (c)(1),
(2) Date: Jan. 20, 2015

(87) PCT Pub. No.: WO2014/024069
PCT Pub. Date: Feb. 13, 2014

(65) Prior Publication Data
US 2015/0182144 A1    Jul. 2, 2015

Related U.S. Application Data

(60) Provisional application No. 61/679,696, filed on Aug. 4, 2012.

(51) Int. Cl.
*A61B 5/06* (2006.01)
*A61B 8/12* (2006.01)
(Continued)

(52) U.S. Cl.
CPC .......... *A61B 5/066* (2013.01); *A61B 1/00009* (2013.01); *A61B 1/00167* (2013.01);
(Continued)

(58) Field of Classification Search
CPC .. A61B 5/00; A61B 8/00; A61B 5/066; A61B 5/0084; A61B 1/00167;
(Continued)

(56) References Cited

U.S. PATENT DOCUMENTS 6,494,835 B1 * 12/2002 Ciezki ................. A61N 5/1002
                                                                     600/439
7,201,715 B2   4/2007 Burdette et al.
(Continued)

FOREIGN PATENT DOCUMENTS

| WO | WO-2011048509 A1 * | 4/2011 | ......... A61B 1/00165 |
| WO | WO 2011080606 A1 * | 7/2011 | ........... A61N 5/1027 |
| WO | WO 2011098926 A1 * | 8/2011 | ........... A61B 8/0841 |

*Primary Examiner* — Sean D Mattson (57) ABSTRACT

A system and method include a shape sensing enabled device (120) including one or more imaging devices (202), the shape sensing enabled device coupled to at fiber (122). A shape sensing module (132) is configured to receive optical signals from the at least one optical fiber within a structure and interpret the optical signals to determine a shape of the shape sensing enabled device. A device positioning module (134) is configured to determine position information of the one or more imaging devices based upon one or more relationships between the at least one optical fiber and the one or more imaging devices. A mapping module (136) is configured to register frames of reference of the at least one optical fiber, the shape sensing enabled device, and a mapping system of a target device (124) to provide an adjusted position of the target device based on the position information.

19 Claims, 3 Drawing Sheets

(51) Int. Cl.
    *A61N 5/10*     (2006.01)
    *A61B 8/08*     (2006.01)
    *A61B 8/00*     (2006.01)
    *A61B 1/00*     (2006.01)
    *A61B 5/00*     (2006.01)
    *A61B 34/20*    (2016.01)

(52) U.S. Cl.
    CPC .......... *A61B 5/0084* (2013.01); *A61B 8/0841* (2013.01); *A61B 8/12* (2013.01); *A61B 8/4254* (2013.01); *A61B 8/4466* (2013.01); *A61N 5/1027* (2013.01); *A61N 5/1049* (2013.01); *A61N 5/1067* (2013.01); *A61B 8/58* (2013.01); *A61B 2034/2061* (2016.02); *A61N 2005/1058* (2013.01)

(58) Field of Classification Search
    CPC . A61B 1/0009; A61B 2034/2061; A61B 8/12; A61B 8/0841; A61B 8/4466; A61B 8/4254; A61B 8/58; A61N 5/00; A61N 2005/00; A61N 5/1049; A61N 5/1067; A61N 5/1027; A61N 2005/1058
    See application file for complete search history.

(56) References Cited

U.S. PATENT DOCUMENTS

| | | | |
|---|---|---|---|
| 7,888,942 | B2 | 2/2011 | Chen et al. |
| 8,622,935 | B1* | 1/2014 | Leo .................. A61B 5/6843 |
| | | | 600/585 |
| 8,983,575 | B2 | 3/2015 | Krueger et al. |
| 9,625,254 | B2 | 4/2017 | Manzke et al. |
| 2007/0265503 | A1* | 11/2007 | Schlesinger ........... A61B 5/065 |
| | | | 600/182 |
| 2008/0275341 | A1* | 11/2008 | Fehre .................. A61N 5/1002 |
| | | | 600/439 |
| 2009/0306644 | A1* | 12/2009 | Mayse .................... A61B 8/12 |
| | | | 606/33 |
| 2010/0030063 | A1* | 2/2010 | Lee ......................... A61B 5/06 |
| | | | 600/424 |
| 2010/0249506 | A1* | 9/2010 | Prisco ................ A61B 1/00009 |
| | | | 600/117 |
| 2011/0166410 | A1* | 7/2011 | Gutierrez ............. A61N 5/1015 |
| | | | 600/8 |
| 2013/0102891 | A1 | 4/2013 | Binnekamp et al. |
| 2013/0131499 | A1 | 5/2013 | Chan et al. |
| 2013/0204072 | B2 | 8/2013 | Verard et al. |
| 2013/0308137 | A1 | 11/2013 | Manzke et al. |
| 2014/0148703 | A1 | 5/2014 | Deladi et al. |
| 2019/0015072 | A1 | 1/2019 | Deladi et al. |

* cited by examiner

QUANTIFYING PROBE DEFLECTION FOR IMPROVED CATHETER IDENTIFICATION

CROSS-REFERENCE TO PRIOR APPLICATIONS

This application is the U.S. National Phase application under 35 U.S.C. § 371 of International Application Serial No. PCT/IB2013/056000, filed on Jul. 22, 2013, which claims the benefit of U.S. Application Ser. No. 61/679,696, filed on Aug. 4, 2012. This application is hereby incorporated by reference herein.

This disclosure relates to medical instruments and more particularly to shape sensing optical fibers in medical applications for improved identification of medical instruments.

High dose rate (HDR) brachytherapy procedures involve the transperineal placement of catheters under transrectal ultrasound (TRUS) guidance. Subsequently, catheter identification using TRUS images is performed manually. However, this leads to a high probability of error, since the ultrasonic speckle combined with the variable echogenicity of the catheters makes it difficult for the catheters to be accurately and consistently identified, resulting in inaccuracies in the treatment planning process. Automated methods of catheter mapping include electromagnetic (EM) tracking of sensors or guidewires placed in the catheter. This method requires a consistently stable relationship between the EM and TRUS frames of reference. However, in clinical situations, the process of positioning the TRUS probe within the patient induces a bending/deflection of the probe, which may cause inconsistencies in the registration of the EM and TRUS frames of reference.

In accordance with the present principles, a system includes a shape sensing enabled device including one or more imaging devices, the shape sensing enabled device coupled to at least one optical fiber. A shape sensing module is configured to receive optical signals from the at least one optical fiber within a structure and interpret the optical signals to determine a shape of the shape sensing enabled device. A device positioning module is configured to determine position information of the one or more imaging devices based upon one or more relationships between the at least one optical fiber and the one or more imaging devices. A mapping module is configured to register frames of reference of the at least one optical fiber, the shape sensing enabled device, and a mapping system of a target device to provide an adjusted position of the target device based on the position information.

A system includes a shape sensing enabled medical device including one or more imaging devices, the shape sensing enabled medical device coupled to at least one optical fiber. A shape sensing module is configured to receive optical signals from the at least one optical fiber within a structure and interpret the optical signals to determine a shape of the shape sensing enabled medical device. A device positioning module is configured to determine position information of the one or more imaging devices based upon one or more relationships between each of the at least one optical fiber and one or more points each representing the one or more imaging devices. The one or more relationships is determined prior to placing the one or more imaging devices within the structure. A mapping module is configured to register frames of reference of the at least one optical fiber, the shape sensing enabled medical device, and a mapping system of a target device to provide an adjusted position of the target device based on the position information.

A method includes collecting shape sensing data from a shape sensing enabled device disposed within a structure, the shape sensing enabled device coupled to at least one optical fiber and including one or more imaging devices. Position information of the one or more imaging devices is determined based upon one or more relationships between the at least one optical fiber and the one or more imaging devices. Frames of reference of the at least one optical fiber, the shape sensing enable device, and a mapping system of a target device are registered to provide an adjusted position of the target device based on the position information.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

In accordance with the present principles, systems and methods for identifying a catheter during an HDR brachytherapy procedure are provided. Typically, HDR brachytherapy is performed under the guidance of transrectal ultrasound (TRUS). However, the insertion of the TRUS probe into a subject induces a deflection/bend in the probe. Fiber optic shape sensing may be applied to quantify the deflection/bend in the probe to thereby provide positional information of the probe. Based on spatial relationships between optical fibers coupled to the probe and the TRUS imaging arrays, positional information of the TRUS imaging arrays may be computed.

Catheters may be mapped using, e.g., optical fibers or electromagnetic (EM) sensors. The frames of references of the TRUS imaging arrays, optical fibers and mapping system of the catheters may be registered. The mapped position of the catheters may be adjusted based on the positional information of the TRUS imaging arrays, representing the true catheter positions with TRUS probe deflection/bending taken into account.

Advantageously, the present principles provide accurate, real-time updates of catheter and afterloader positions (and hence, radioactive source positions). The ability to provide real-time source position updates may reduce the disconnect between treatment planning and delivery, which may exist due to inconsistent spatial relationships between the treatment sources and tissue. Real-time catheter tracking during treatment delivery may also allow for treatment adaptation.

It also should be understood that the present invention will be described in terms of medical instruments; however, the teachings of the present invention are much broader and are applicable to any fiber optic or imaging instruments. In some embodiments, the present principles are employed in tracking or analyzing complex biological or mechanical systems. In particular, the present principles are applicable to internal tracking procedures of biological systems, procedures in all areas of the body such as the lungs, gastrointestinal tract, excretory organs, blood vessels, etc. The elements depicted in the figures may be implemented in various combinations of hardware and software and provide functions which may be combined in a single element or multiple elements.

The functions of the various elements shown in the figures can be provided through the use of dedicated hardware as well as hardware capable of executing software in association with appropriate software. When provided by a processor, the functions can be provided by a single dedicated processor, by a single shared processor, or by a plurality of individual processors; some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
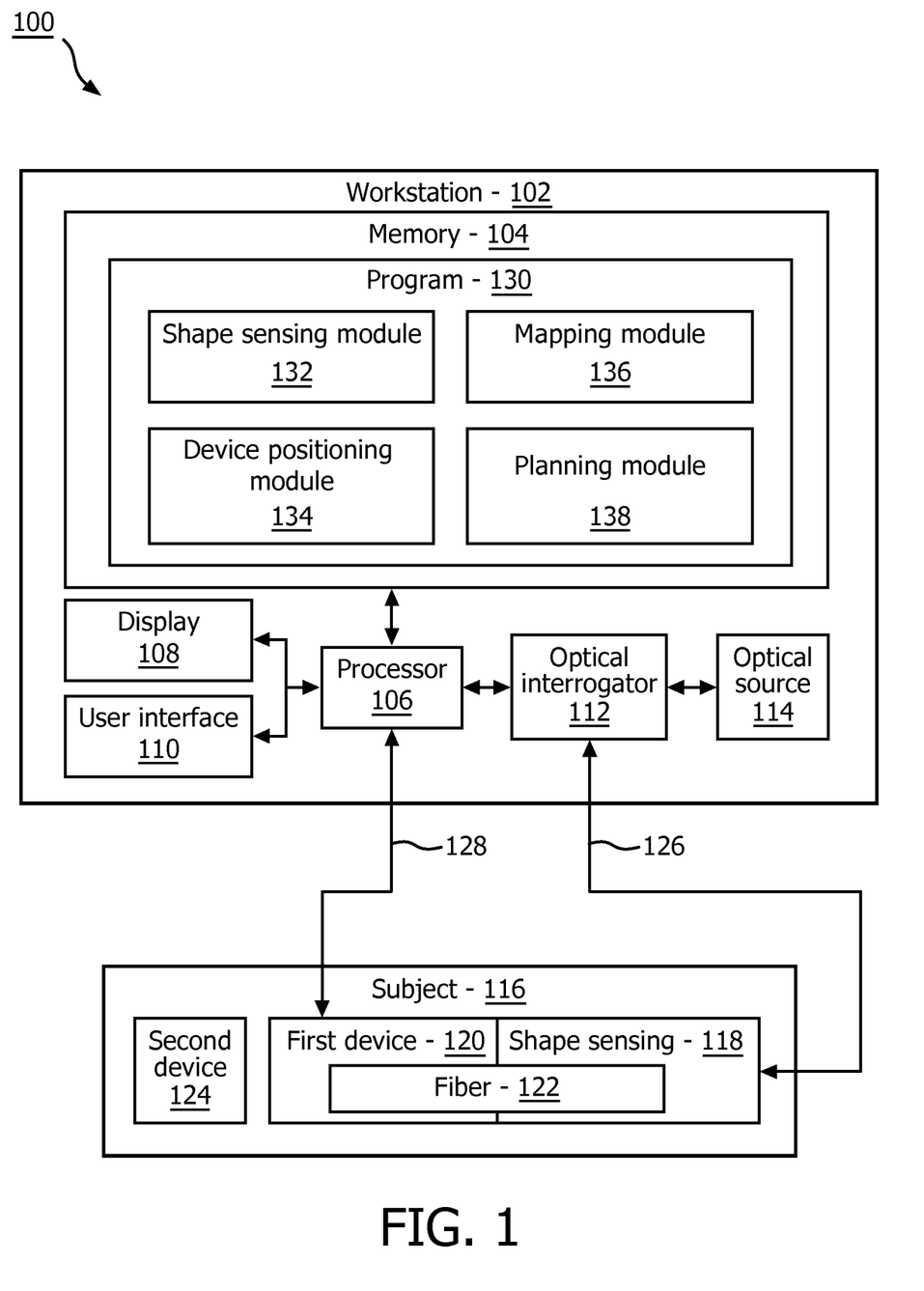
FIG. 1 is a block/flow diagram showing a shape sensing system to identify a position of a device in accordance with one embodiment.

Referring now to the drawings in which like numerals represent the same or similar elements and initially to FIG. 1, a system 100 for determining positioning information of a catheter is illustratively depicted in accordance with one embodiment. The system 100 may include a workstation or console 102 from which procedures (e.g., HDR brachytherapy) are supervised and managed. Workstation 102 preferably includes one or more processors 106 and memory 104 for storing programs and applications. It should be understood that the functions and components of system 100 may be integrated into one or more workstations or systems.

Workstation 102 may include one or more displays 108 for viewing. The display 108 may also permit a user to interact with the workstation 102 and its components and functions. This is further facilitated by a user interface 110, which may include a keyboard, mouse, joystick, or any other peripheral or control to permit user interaction with the workstation 102.

While the present principles will be described with respect to an HDR brachytherapy procedure, one of ordinary skill in the art would recognize that the present principles are much broader and may be applicable to any workflow utilizing an imaging system that communicates between multiple tracking systems. For example, the present principles may be applied to create flexible ultrasound arrays or other imaging devices that conventionally need to be rigid in order to have a known imaging geometry. Tracking with optical shape sensing provides real-time knowledge of the specific geometry of a flexible imaging device, which enables access to areas or structures that are difficult to image with conventional, rigid devices. In another example, the present principles may be applied in plumbing where pipes may be imaged using both an ultrasound system and an endoscope. Other applications are also contemplated.

Memory 104 may store a computer implemented program 130 including a shape sensing module 132 configured to interpret optical feedback signals from a shape sensing device or system 118. Shape sensing module 132 is configured to use the optical signal feedback (and any other feedback, e.g., electromagnetic (EM) tracking) to reconstruct deformations, deflections and other changes associated with a first medical device or instrument 120. The first device 120 preferably includes a (e.g., transrectal ultrasound (TRUS)) probe, but may include one or more of an endoscope, or other imaging components, etc. The probe 120 may be coupled to the workstation 102 through cabling 128. The cabling 128 may include electrical connections, optical fiber connections, instrumentation, etc., as needed. The probe 120 may be used to evaluate a structure or subject 116 (e.g., patient).

A shape sensing system includes module 132 and shape sensing device 118 mounted on or integrated into the probe 120. The shape sensing system includes an optical interrogator 112 that provides selected signals and receives optical responses. An optical source 114 may be provided as part of the interrogator 112 or as a separate unit for providing light signals to the shape sensing device 118. Shape sensing device 118 includes one or more optical fibers 122 which may be coupled to the device 120 in a set pattern or patterns. The fibers 122 may be coupled to the workstation 102 through cabling 126. The cabling may include fiber optics, electrical connections, other instrumentation, etc. as needed.

In one embodiment, the fibers 122 are integrated within the casing of the probe 120. If multiple fibers 122 are utilized, each fiber 122 may be arranged in a specific pattern around the circumference or perimeter of the probe 120, with each fiber 122 running along the length of the probe 120.

Figure 2:
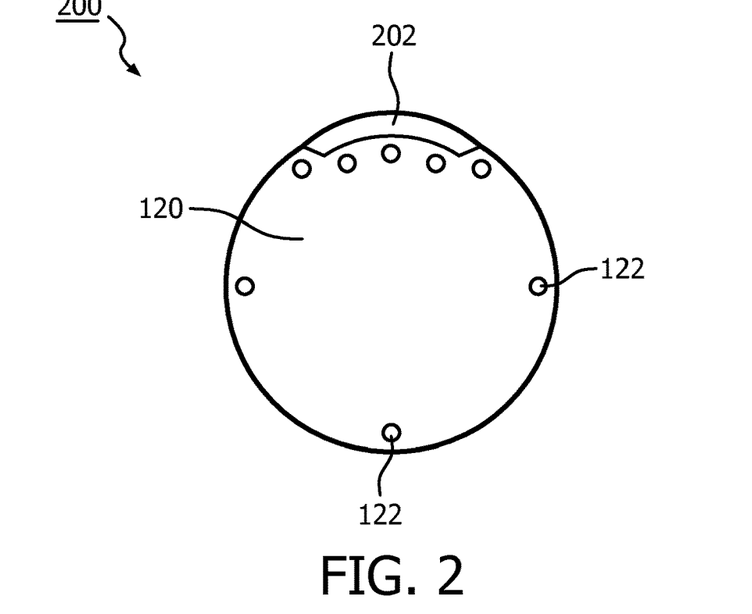
FIG. 2 illustratively depicts a cross-sectional view of a probe including an exemplary arrangement of optical fibers in accordance with one embodiment.

Referring for a moment to FIG. 2, with continued reference to FIG. 1, a cross-sectional view of a TRUS probe 200 including an exemplary arrangement of optical fibers is illustratively depicted in accordance with one embodiment. Since deflection of the probe 120 may be non-linear, it may be advantageous to have a greater concentration of fibers 122 placed in close proximity to the one or more imaging arrays 202 of the probe 120, with a sparser distribution of fibers 122 away from the imaging arrays 202. Other patterns of fibers 122 within the probe 120 are also contemplated. For example, a distribution of fibers 122 throughout the cross-section of the probe 120 may offer several advantages: the capability to measure relative positions of multiple fibers 122 with respect to each other; and providing measurement redundancy in the event that communication with one or more of the fibers 122 fails. However, if the positions of fibers 122 change, the spatial relationship between the fibers 122 and imaging arrays 202 may not be valid either.

Referring back to FIG. 1, in another embodiment, the fibers 122 may be externally coupled to the probe 120 using, e.g., a clip-on attachment. The fibers 122 are rigidly registered to the probe 120. While this embodiment may limit the proximity of the fibers 122 to the imaging arrays of the probe 120, it affords some flexibility to the operator with regards to the placement of the fibers 122. Other arrangements of the fibers 122 coupled on or in the probe 120 are also contemplated.

Shape sensing 118 with fibers 122 may be implemented using any mechanism of optical fiber transmission/reflection. For example, shape sensing 118 with fibers 122 may be implemented using one or more of: wavelength-division multiplexed distributed sensing, time-wavelength-division multiplexed distributed sensing, interferometric detection, amplitude-based inherent scattering, etc. Preferably, shape sensing 118 with fibers 122 is based on the fiber optic Bragg grating (FBG) principle; however, other approaches are also contemplated, such as, e.g., Rayleigh scattering, Raman scattering or Brillouin scattering. FBG is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

The shape of the fibers 122 at any spatial location along its length is dependent on the internal strain developed in the fiber. The Bragg wavelength is sensitive to this strain. Shape sensing module 132 may use the strain in three or more FBGs (one in each fiber 122, in a group of three fibers 122) to calculate the local bend in the fiber group. Thus, the shape of the fiber is accumulated. A priori knowledge of the FBG positions along the fiber can be utilized to provide shape and position estimates of the fiber in the desired frame of reference.

Computer implemented program 130 may include a device positioning module 134 configured to determine the origins of the imaging array of the probe 120 upon insertion into the subject 116. Initially, prior to positioning the probe 120 within the subject 116, device positioning module 134 may compute a transformation between the fibers 122 and the imaging arrays of the probe 120. The transformation represents spatial relationships between the fibers 122 and the imaging arrays of the probe 120 for an unbent configuration of the probe 120. In one embodiment, spatial relationships are defined between each fiber 122 and one or more points (e.g., center) each representing the one or more imaging arrays of the probe 120. In another embodiment, fibers 122 are divided into multiple sections and spatial relationships are defined between each section of each fiber 122 and the center of each of the imaging arrays of probe 120. Other embodiments are also contemplated. The spatial relationships are constant throughout the procedure. If not, recalibration may be performed.

Preferably, spatial relationships are determined in a pre-procedural calibration step, prior to the probe 120 insertion into subject 116. For example, the pre-procedural calibration may be a one-time calibration performed intermittently (e.g., weekly, monthly, etc.). This calibration step allows the origins of the imaging arrays of the probe 120 to be defined relative to the coordinate system of the fibers 122. In another embodiment, a prior pre-procedural calibration may be adjusted intra-procedurally.

Once the probe 120 has been positioned and stabilized within the subject 116, the shape and pose of each of the fibers 122 is recorded using shape sensing module 126. Based upon the determined spatial relationship between fibers 122 and the imaging arrays of the probe 120, device positioning module 134 may compute the origins of the imaging arrays of the probe 120. The origins of the imaging arrays are preferably stored in memory 104 in a common frame of reference (e.g., the probe's 120 frame of reference).

Figure 3:
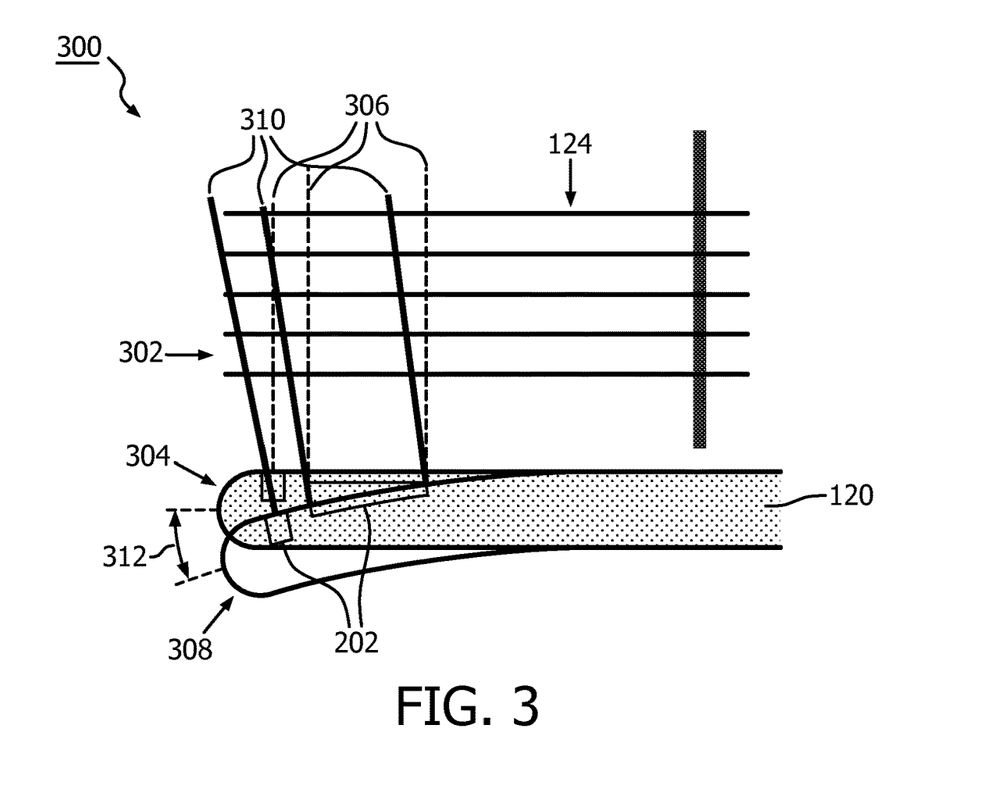
FIG. 3 illustratively depicts the effect of probe deflection/bending when positioned within a subject.

Referring for a moment to FIG. 3, a probe 300 is positioned within a subject. Prior to positioning the probe 120 within a subject 116, for an unbent configuration 304 of the probe, a target area 302 of a subject 116 is imaged 306 with no probe deflection/bending. However, the process of positioning the probe 120 in the subject 116 induces a bending/deflection 312. The bent probe 308 images 310 the target area 302. Using spatial relationships between fibers 122 coupled to the probe 120 and the imaging arrays 202 of the probe 120, the device positioning module 134 may account for the bending/deflection 312 to compute the origins of the imaging arrays.

Referring back to FIG. 1, the computer implemented program 130 may include a mapping module 136 configured to map the position of one or more second medical devices or instruments 124 within the subject 116 prior to treatment planning. The second device 124 preferably includes a catheter, but may include one or more of a probe, a guidewire, an endoscope, a robot, an electrode, a filter device, a balloon device, or other components, etc. The catheters 124 may be positioned within the subject 116 for, e.g., HDR brachytherapy.

In one embodiment, the mapping module 136 is configured to perform EM-based path mapping to identify the catheter 124 positions within the subject 116. In an embodiment, EM-based path mapping may be performed using an EM-tracked guidewire that can be inserted into and retracted from catheters 124. The spatial information of the tracker may be recorded during this process. Other embodiments of EM-based path mapping are also contemplated. The frames of reference of the EM system, fibers 118 and imaging arrays of the probe 120 are registered. In another embodiment, the mapping module 136 may be configured to perform optical shape sensing to identify the catheter 124 positions within the subject 116. The frames of reference of the fibers 122 (used in both the catheters 124 and the probe 120) and the imaging arrays of the probe 120 are registered. Other embodiments of mapping the catheter 124 within the subject 116 are also contemplated.

The mapping module 136 may adjust the position information of the catheter 124 based on the origins of the imaging arrays of the probe 120, determined by device positioning module 134. The adjusted catheter 124 positions represent the true catheter 124 positions determined with deflection/bending of the probe 120 taken into account.

The mapping module 136 may be further configured to perform real-time catheter 124 tracking during a procedure, such as treatment delivery. If the catheter 124 shape and pose are tracked using fibers 122, then real-time changes in the shape of the catheters 124 can be determined and adjusted based on the calculated deflection/bending of the probe 120 at that time instant. Each incremental position of the afterloader device within the catheters 124 can also be recorded to provide a real-time estimate of the positions of the radioactive sources. Advantageously, by knowing the planned locations of the radioactive sources, real-time adaptions can be made to the treatment plan.

The computer implemented program 130 may also include a planning module 138. The planning module may involve one or more displays 108 and/or user interfaces 110. In one embodiment, the planning module 138 may be configured to provide pre-planning mapping of catheters 124, such as in an, e.g., HDR brachytherapy procedure. Knowledge of the position of the imaging arrays of the probe 120 allows for improved accuracy in the estimates of catheter positions, which are used to formulate an initial treatment plan to specify appropriate dose levels for target areas and/or surrounding organs at risk (OARs).

In another embodiment, the planning module 138 may provide for adaptive treatment planning using real-time updates of catheter 124 and afterloader positions. In the event of catheter 124 motion (relative to the target area of the subject 116), the initial treatment plan may be modified to account for the motion. For example, if the estimated dose received by the target is less than the planned dose in the, e.g., posterior region of the target, then the dwell positions and dwell times of sources in the catheters closes to the posterior region of the target can be adjusted accordingly to compensate for the reduced dosage in that region. Other modifications to the treatment plan are also contemplated.

Figure 4:
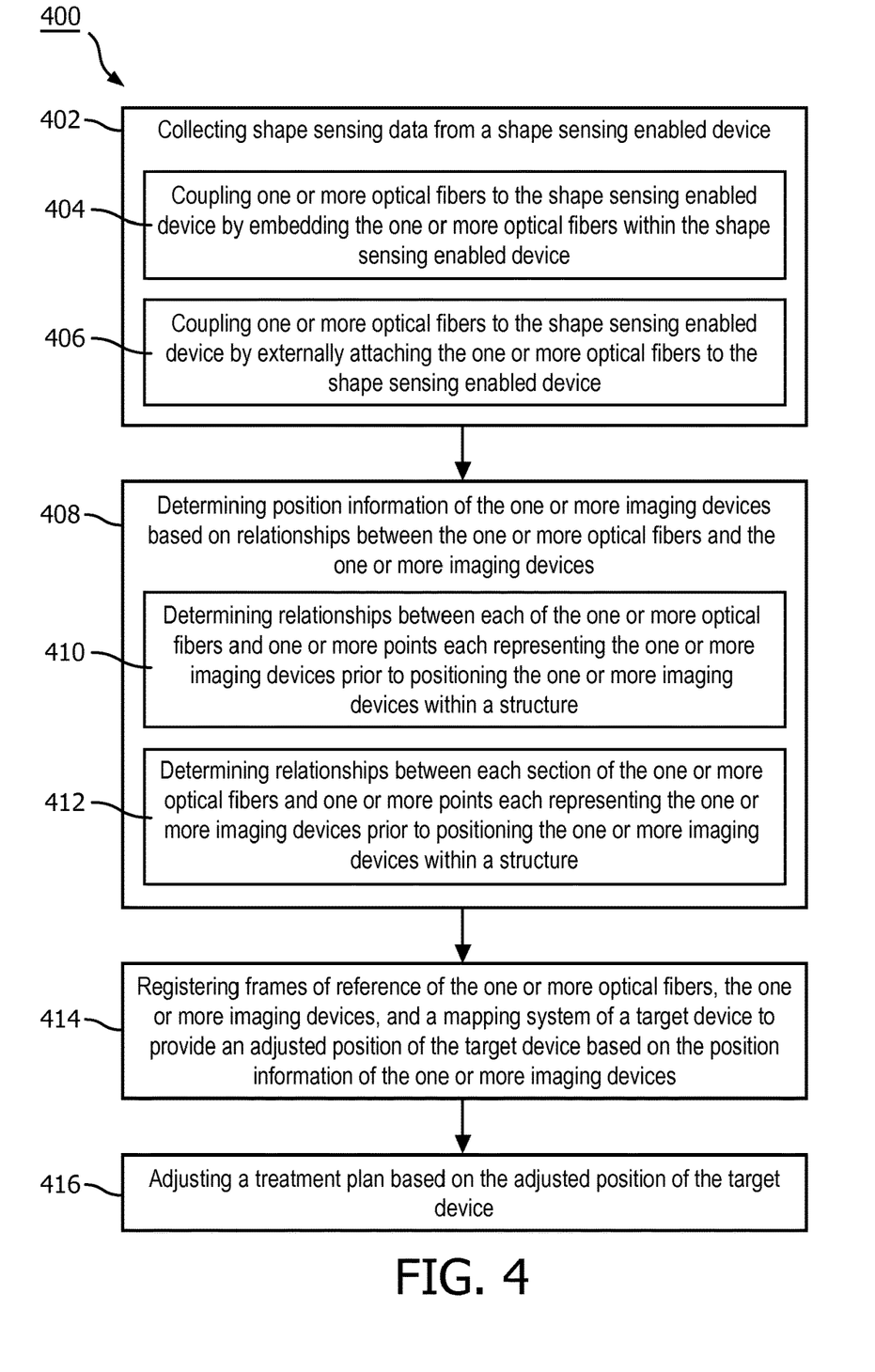
FIG. 4 is a block/flow diagram showing a method for identifying a position of a device in accordance with one embodiment.

Referring now to FIG. 4, a block diagram showing a method for determining positioning information of a catheter is illustratively depicted in accordance with one embodiment. In block 402, shape sensing data is collected from a shape sensing enabled device. The shape sensing enabled device preferably includes an ultrasound probe, but may also include an endoscope, or other imaging components, etc. The shape sensing enabled device may be disposed within a structure, such as, e.g., a vascular structure, a mechanical structure, etc.

One or more optical fibers are preferably coupled to the shape sensing enabled device in a set pattern or patterns. In one embodiment, in block 404, the optical fibers may be integrated or embedded within the shape sensing enabled device. For example, the optical fibers may be arranged such that a greater concentration of optical fibers is positioned in close proximity to one or more imaging devices (e.g., imaging arrays) of the shape sensing enabled device, with a sparser distribution of optical fibers away from the imaging devices. In another example, optical fibers may be distributions throughout the cross-section of the shape sensing enabled device. In still another embodiment, in block 406, the optical fibers may be externally coupled to the shape sensing enabled device using, e.g., a clip on attachment. Other patterns of positioning optical fibers in or around the shape sensing enabled device are also contemplated.

In block 408, position information of the imaging devices of the shape sensing enabled device is determined based on spatial relationships between the fibers and the one or more imaging devices. Initially, prior to the disposition of the shape sensing enabled device within the structure, a transformation between the fibers and imaging devices of the shape sensing enabled device is determined. The transformation represents spatial relationships between the fibers and the imaging devices. In one embodiment, in block 410, spatial relationships are defined between each fiber and one or more points (e.g., center) each representing the one or more imaging devices of the shape sensing enabled device. In another embodiment, in block 412, fibers are divided into multiple sections and spatial relationships are defined between each section of each fiber and one or more points each representing the one or more imaging devices of the shape sensing enabled device. Other embodiments are also contemplated. The spatial relationships are constant throughout the procedure. If not constant, recalibration may be performed.

Preferably, spatial relationships are determined in a pre-procedural calibration step, prior to the disposition of the shape sensing enabled device within the structure. For example, the pre-procedural calibration may be a one-time calibration performed intermittently (e.g., weekly, monthly, etc.). This calibration step allows the origins of the imaging devices of the shape sensing enabled device to be defined relative to the coordinate system of the fibers.

Once the shape sensing enabled device has been positioned within the structure, the shape and pose of the fibers are recorded. Based on the spatial relationship between the fibers and the one or more imaging devices, position information of the one or more imaging devices of the shape sensing enabled device may be determined.

In block 414, frames of reference of the optical fibers, imaging devices, and a mapping system of a target device are registered to provide an adjusted position of the target device based on the position information of the imaging devices. The target device preferably includes a catheter, but may also include a probe, endoscope, guidewire, etc. The target device is mapped using the mapping system. In one embodiment, the mapping system includes an EM-based mapping system. EM-based mapping may be performed using an EM-tracked guidewire. Other methods of EM-based mapping are also contemplated. In another embodiment, the mapping system includes an optical shape sensing system. Other implementations of the mapping system are also contemplated.

The mapped position of the target device (using the mapping system) is adjusted using the position of the imaging devices. The adjusted position of the target device represents the true position determined by taking into account deflection/bending of the shape sensing enabled device.

In block 416, a treatment plan is created or modified. If the target device is tracked using optical fibers, real-time changes in the shape of the target device can be determined and a treatment plan can be adjusted. In one embodiment, a position of an afterloader within a shape sensing enabled device may be recorded to provide a real-time estimate of the positions of (e.g., radioactive) sources positioned in the shape sensing enabled device. Knowing the planned locations of the radioactive sources, real-time adaptations can be made to a treatment plan. For example, if the estimated dose received by the target is less than the planned dose in the, e.g., posterior region of the target, then the dwell positions and dwell times of sources in the target device closest to the posterior region of the target can be adjusted accordingly to compensate for the reduced dosage in that region. Other modifications to the treatment plan are also contemplated.

In another embodiment, a treatment plan may be developed. Knowledge of the position of imaging devices of the shape sensing enabled device results in improved accuracy of the estimates of the position of the target device. Accurate positioning of the target device may be important in the creation of the initial treatment plan.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for quantifying probe deflection for improved catheter identification (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system, comprising:
a shape sensing enabled device having a body which includes one or more imaging devices and a plurality of optical fibers that are distributed through a length of the shape sensing enabled device, wherein there is a greater concentration of the optical fibers in portions of the shape sensing enabled device which are closer to the one or more imaging devices than in portions which are farther away from the one or more imaging devices;
a shape sensing module configured to receive optical signals from the plurality of optical fibers and to interpret the optical signals to determine a shape of the shape sensing enabled device;
a device positioning module configured to determine position information of the one or more imaging devices based upon: (1) spatial relationships between the plurality of optical fibers and the one or more imaging devices, and (2) the determined shape of the shape sensing enabled device; and
a mapping module configured to register frames of reference of the plurality of optical fibers, the one or more imaging devices, and a mapping system of a target device, wherein the mapping system of the target device determines a mapped position of the target device,
wherein the mapping module is configured to provide an adjustment of the mapped position of the target device to determine a true position of the target device, wherein the adjustment is based on the position information of the one or more imaging devices, and wherein the true position takes into account deflection and/or bending of the shape sensing enabled device.

2. The system as recited in claim 1, wherein the shape sensing enabled device is coupled to the plurality of optical fibers by embedding the plurality of optical fibers in the shape sensing enabled device or externally attaching the plurality of optical fibers to the shape sensing enabled device.

3. The system as recited in claim 1, wherein the plurality of optical fibers are distributed throughout a cross-section of the shape sensing enabled device.

4. The system as recited in claim 1, wherein the plurality of optical fibers are arranged around a perimeter of the shape sensing enabled device.

5. The system as recited in claim 1, wherein the device positioning module is further configured to determine the spatial relationships between the plurality of optical fibers and the one or more imaging devices prior to placing the one or more imaging devices within a structure.

6. The system as recited in claim 1, wherein each of the optical fibers has a plurality of sections, and wherein the device positioning module is further configured to determine relationships between each section of the each of the plurality of optical fibers and the one or more imaging devices prior to placing the one or more imaging devices within a structure.

7. The system as recited in claim 1, further comprising a planning module configured to adapt or create a treatment plan for a structure according to the true position of the target device.

8. The system of claim 7, wherein the target device includes a radioactive source and wherein the planning module is further configured to base an exposure time for the radioactive source in the structure on a proximity of the radioactive source to a predetermined location within the structure.

9. The system as recited in claim 1, wherein the mapping system includes at least one of an electromagnetic tracking system and a shape sensing system.

10. The system as recited in claim 1, wherein the shape sensing enabled device includes one or more of a probe and an endoscope.

11. The system as recited in claim 1, wherein the target device includes one or more of a probe, a catheter, a guidewire, and an endoscope.

12. The system as recited in claim 1, wherein the true position takes into account the deflection and/or bending of the shape sensing enabled device when the shape sensing enabled device is inserted in a body cavity.

13. The system of claim 1, wherein the body of the shape sensing enabled device is flexible, and wherein the one or more imaging devices include an imaging array.

14. The system of claim 1, wherein the shape sensing module is further configured to interpret the optical signals using a process selected from the group consisting of wavelength-division multiplexed distributed sensing, time-wavelength-division multiplexed distributed sensing, interferometric detection, amplitude-based inherent scattering, Rayleigh scattering, Raman scattering, and Brillouin scattering.

15. A system, comprising:
a shape sensing enabled medical device having a body which includes one or more imaging devices and a plurality of optical fibers that are distributed through a length of the shape sensing enabled device, wherein there is a greater concentration of the optical fibers in portions of the shape sensing enabled device which are closer to the one or more imaging devices than in portions which are farther away from the one or more imaging devices;
a shape sensing module, wherein the shape sensing module is configured to receive optical signals from the plurality of optical fibers while the one or more imaging devices are disposed within a structure, and wherein the shape sensing module is configured to interpret the optical signals to determine a shape of the shape sensing enabled medical device;

a device positioning module configured to determine position information of the one or more imaging devices based upon: (1) spatial relationships between the plurality of optical fibers and one or more points representing the one or more imaging devices, and (2) the determined shape of the shape sensing enabled device, wherein the spatial relationships are determined prior to placing the one or more imaging devices within the structure; and a mapping module configured to register frames of reference of the plurality of optical fibers, the one or more imaging devices, and a mapping system of a target device, wherein the mapping system of the target device determines a mapped position of the target device, wherein the mapping module is configured to provide an adjustment of the mapped position of the target device to determine a true position of the target device, wherein the adjustment is based on the position information of the one or more imaging devices, and wherein the true position takes into account deflection and/or bending of the shape sensing enabled device.

16. A method, comprising:

collecting shape sensing data from a shape sensing enabled device which includes one or more imaging devices disposed within a structure, wherein the shape sensing enabled device has a body and is coupled to a plurality of optical fibers, and wherein the plurality of optical fibers are distributed through a length of the shape sensing enabled device, with a greater concentration of optical fibers in portions of the shape sensing enabled device which are closer to the one or more imaging devices than in portions which are farther away from the one or more imaging devices;

receiving optical signals from the plurality of optical fibers;

interpreting the optical signals to determine a shape of the shape sensing enabled device;

determining position information of the one or more imaging devices based upon: (1) spatial relationships between the plurality of optical fibers and the one or more imaging devices, and (2) the determined shape of the shape sensing enabled device;

registering frames of reference of the plurality of optical fibers, the one or more imaging devices, and a mapping system of a target device, wherein the mapping system of the target device determines a mapped position of the target device; and providing an adjustment of the mapped position of the target device to determined a true position of the target device, wherein the adjustment is based on the position information of the one or more imaging devices, and wherein the true position takes into account deflection and/or bending of the shape sensing enabled device.

17. The method as recited in claim 16, wherein determining position information further includes determining the spatial relationships between the plurality of optical fibers and the one or more imaging devices prior to placing the one or more imaging devices within the structure.

18. The method of claim 16, wherein the target device includes a radioactive source, and further comprising treating a patient with an exposure time for the radioactive source in the structure that is based on a proximity of the radioactive source to a predetermined location within the structure.

19. The method of claim 16, wherein the shape sensing data is interpreted using a process selected from the group consisting of wavelength-division multiplexed distributed sensing, time-wavelength-division multiplexed distributed sensing, interferometric detection, amplitude-based inherent scattering, Rayleigh scattering, Raman scattering, and Brillouin scattering.

* * * * *